United States Patent [19]

Whitley

[11] 4,289,855
[45] Sep. 15, 1981

[54] SAFETY CATALYST SYSTEMS

[75] Inventor: Donald C. Whitley, Shipley, England

[73] Assignee: Oxoid Limited, Basingstoke, England

[21] Appl. No.: 971,830

[22] Filed: Dec. 19, 1978

[30] Foreign Application Priority Data

Dec. 30, 1977 [GB] United Kingdom ............... 54354/77

[51] Int. Cl.³ .......................... B01J 8/02; B01J 35/04
[52] U.S. Cl. .................................. 435/287; 422/117;
422/211; 435/299; 435/801
[58] Field of Search .................. 422/177–179,
422/181, 211, 240, 171, 241, 117; 435/287, 299,
801; 29/157 R, 163.5 R, 163.5 CW; 252/477 R,
477 Q; 423/210 C, 219, 248

[56] References Cited
U.S. PATENT DOCUMENTS

| | | | |
|---|---|---|---|
| 1,953,120 | 4/1934 | Miller | 422/171 |
| 3,295,919 | 1/1967 | Henderson et al. | 422/177 |
| 3,369,859 | 2/1968 | Cornelius | 423/219 |
| 3,483,089 | 12/1969 | Brewer | 435/287 |
| 3,713,281 | 1/1973 | Asker et al. | 422/211 |
| 3,889,464 | 6/1975 | Gardner | 422/178 |
| 3,925,252 | 12/1975 | Yabuta et al. | 422/177 |
| 3,948,810 | 4/1976 | Hervert | 252/477 R |

Primary Examiner—Bradley Garris
Attorney, Agent, or Firm—Wenderoth, Lind & Ponack

[57] ABSTRACT

Safety catalyst systems and their use in chemical reactions carried out in the gas phase, wherein the safety catalyst system comprises pelleted catalyst held loose in and throughout the holes and folds of a folded or rolled up metal foil net which is inside a container having holes for the inflow and outflow of gases. The safety catalyst system of the invention does not allow the formation of localized hot-spots or allow free catalyst dust to escape from the system, both of which are known disadvantages of prior art systems.

9 Claims, 2 Drawing Figures

SAFETY CATALYST SYSTEMS

This invention relates to safety catalyst systems for performing chemical reactions in the gas phase.

The atmosphere in an anaerobic jar for culturing anaerobic microorganisms requires deoxygenation. One method of doing this is to introduce hydrogen into the atmosphere in a closed and sealed anaerobic jar and then to react the hydrogen and the oxygen to produce water.

This reaction needs to be carried out quickly and efficiently. At elevated temperatures the reaction is explosive, and at low temperatures the reaction is slow. The reaction at room temperature under such conditions is traditionally catalyzed by palladium metal.

J. H. Brewer and D. L. Allgeier, Applied Microbiology 14 p. 985-8 1966 describe a carbon dioxide-hydrogen anaerobic system wherein attached to the underside of the lid of the jar is a catalyst system. This system comprises a wire gauze catalyst holder containing small pellets of catalyst carrier surface-covered with palladium. The gauze holder is further enclosed within but not in contact with a wire mesh flash arrestor.

The reaction between hydrogen and oxygen in the presence of a catalyst is strongly exothermic and, consequently, the catalyst and the holder system becomes very hot. The individual catalyst pellets in contact with the holder produce localized "hot-spots". These "hot-spots" cause damage to the gauze holder and the heat produced may damage the anaerobic jar and the contents therein. More important, however, the pellets or, in particular, dust generated by the pellets rubbing together may cause an explosion when in contact with the atmosphere in an anaerobic jar without the benefit of a heat sink.

Another catalyst system that has been tried comprises a gauze sachet containing the loose pelleted catalyst. The major disadvantage of this system is that dust generated by the catalyst pellets rubbing together escapes from the gauze sachet. This catalyst dust in free contact with the oxygen/hydrogen mixture may achieve a temperature of above 400° C. by virtue of the exothermic reaction. At this temperature an explosive reaction is a serious danger. In both of these described systems a further problem is caused by clumping of the pellets, thus reducing the efficiency of the system.

One object of the invention is to provide a safety catalyst for use in gaseous reactions. Another object is to provide a catalyst system for use in anaerobic jars containing hydrogen and oxygen.

The invention provides a safety catalyst system for use in gaseous reactions wherein the safety catalyst system comprises pelleted catalyst held loose in and throughout the holes and folds of a folded or rolled up metal foil net which is inside a container having holes for the inflow and outflow of gases.

The use of the metal foil net overcomes the disadvantages found with the catalyst systems described in the prior art.

The advantages of the catalyst system of the present invention are listed as follows:

(a) the foil net acts as a heat sink as it conducts away the heat produced by the reaction at the reaction sites, i.e. at the catalyst pellets, thus preventing the formation of localized "hot-spots", (b) the foil net wrapped around inside the outer container acts as a cushioning device for the pelleted catalyst. The pellets are prevented from rubbing together to produce a potentially dangerous dust; however, any dust or chippings that are produced are held and restrained by the foil net and do not escape, (c) the pelleted catalyst is also for the most part held away from the outer container, thus reducing the amount of deterioration of the container walls, (d) the loose distribution of the catalyst pellets within and throughout the foil net allows good gas circulation through the system. The reaction is, therefore, quick and complete.

The substance useful as the catalyst material may be any known catalytically-active substance. This substance may itself be pelleted or may be coated on some other pelleted substance acting as a carrier.

A particularly effective catalyst is palladium metal coated on alumina pellets.

To reduce the number of sharp edges on the catalyst pellets that might break or chip and produce a dangerous dust, and also to provide a large catalytically-active surface area it is preferred that the catalyst pellets are spherical.

The metal foil net may be formed from any heat-conducting metal foil that is inert to the particular conditions used.

A particularly effective and economical metal for use in the foil net is aluminium, e.g. as expanded or stretched sheet.

The foil net useful in this invention is formed from a metal sheet punched with slots of length of about 0.5 to 2 cm which may be expanded before or during wrapping around the catalyst pellets. Preferably the slots are about 1 cm in length.

Preferably, the ratio of foil net to catalyst is not less than 0.75:1 by weight.

The outer container can be made from any suitable material that is heat resistant, heat conducting and inert to the reaction conditions employed. Preferably, the outer container is a bag, sachet or envelope formed from a steel gauze or fine mesh which preferably has spark shield or flame retardant properties.

In use the catalyst system is attached to a reaction chamber and is, preferably, in contact with a metal wall or lid of the chamber which will allow the heat of reaction at the catalyst to dissipate.

The catalyst system is particularly useful and effective when used in a hydrogen anaerobic system to catalyze the reaction between hydrogen and oxygen.

The risk of explosion in the anaerobic jar and the risk of damage to contents therein is reduced by the use of the catalyst system described herein.

EXAMPLE

A preferred safety catalyst system according to the present invention is shown diagrammatically in FIGS. 1 and 2.

Figure 1:
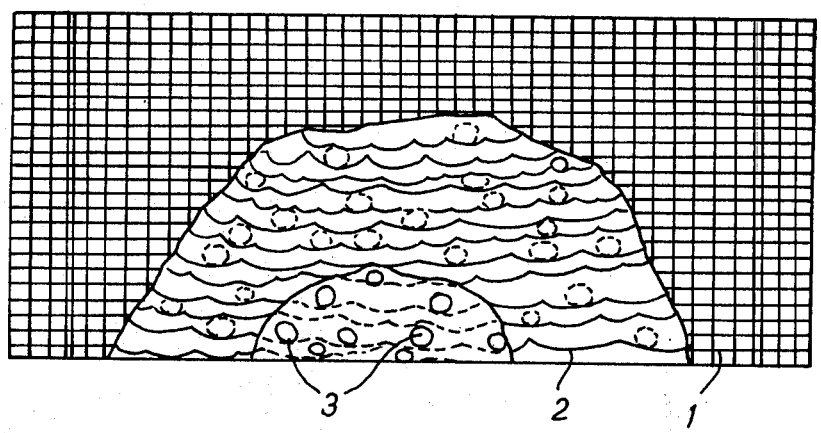
FIG. 1 shows a plan view partly cut away to show the interior.
Figure 2:
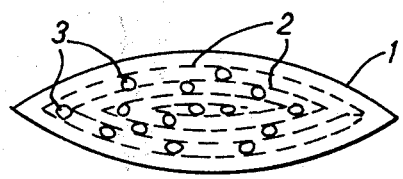
FIG. 2 shows a cross-section of the same arrangement.

A gauze outer envelope (1) formed from stainless steel grade 304 (A1S1) wire having a diameter of 125 microns and wherein the gauze contains, per linear inch, 70 apertures of size 236 microns completely surrounds a volume of 45 cc containing a rolled up and folded length of slit aluminium sheet (2) sold under the Trade Mark "EXPLOSAFE", constituting the metal foil net, having holes of side 1 cm. The sheet (2) contains, dispersed throughout, small alumina spheres of approximately 3 mm diameter coated with palladium metal (3). The aluminium sheet is formed with transverse slots 1 cm long. The action of folding and wrapping it round the catalyst spheres partly stretches the sheet and expands the slots into holes. The weight of catalyst spheres used in the system is 4 g and the weight of expanded aluminium foil used is 3 g.

The pellets are held and cushioned one from the other in intimate contact with a heat-sink material which prevents a rise in temperature above 150° C. within an anaerobic jar, which may contain an explosive mixture of oxygen and hydrogen, thus eliminating any possibility of explosion.

The expanded aluminium foil together with the stainless steel wire gauze outer envelope, prevents the possibility of particles of catalyst from the carrier surface dropping out into the jar.

I claim:

1. In a system comprising an anaerobic jar containing an explosive mixture of oxygen and hydrogen and a catalytic device for catalyzing a reaction between the oxygen and hydrogen, the improvement wherein said catalytic device comprises: a container having holes for the inflow and outflow of gases, a metal foil net folded or rolled up inside said container, and a pelleted catalyst held loose in and throughout the holes and folds of said metal foil net, the ratio of metal foil net to catalyst being not less than 0.75:1 by weight, whereby said metal foil net constitutes a heat-sink material which, by preventing the formation of localized hotspots, reduces the risk of an explosion between the oxygen and hydrogen.

2. The improvement according to claim 1 wherein the metal foil net constitutes a heat-sink material which prevents a temperature rise above 150° C. within said anaerobic jar.

3. The improvement according to claim 1, wherein the metal foil net is formed from a metal sheet punched with slots of length of about 0.5 to 2 cm and then expanded.

4. The improvement according to claim 3, wherein the slots are about 1 cm in length.

5. The improvement according to claim 3, wherein the metal sheet is made of aluminium.

6. The improvement according to claim 1, wherein the container is in the form of a bag, sachet or envelope formed from steel gauze or fine mesh.

7. The improvement according to claim 6, wherein the steel gauze or fine mesh has spark shield or flame retardant properties.

8. The improvement according to claim 1, wherein the pelleted catalyst is palladium metal coated on alumina pellets.

9. The improvement according to claim 8, wherein the pellets are spherical.

* * * * *